United States Patent [19]

Nunami et al.

[11] Patent Number: 5,523,313

[45] Date of Patent: Jun. 4, 1996

[54] INDOLE-CONTAINING PEPTIDE AND PROCESS FOR PREPARING THE SAME

[75] Inventors: Ken-ichi Nunami, Kobe; Koji Yano, Kitamoto, both of Japan; Kenji Omori, Paris, France

[73] Assignee: Tanabe Seiyaku Co., Ltd., Osaka, Japan

[21] Appl. No.: 264,061

[22] Filed: Jun. 22, 1994

[51] Int. Cl.$^6$ .................... A61K 31/425; C07D 277/22
[52] U.S. Cl. .................... 514/365; 514/374; 514/19; 548/201; 548/235
[58] Field of Search .................... 548/201, 235; 514/19, 365, 374

[56] References Cited

U.S. PATENT DOCUMENTS

| | | | |
|---|---|---|---|
| 2,491,523 | 12/1949 | Sheehan et al. | 260/302 |
| 2,538,963 | 1/1951 | Dutcher et al. | 260/302 |
| 3,804,820 | 4/1974 | Quitt et al. | 260/112.5 |
| 4,313,945 | 2/1982 | Wiederkehr et al. | 424/246 |
| 4,331,806 | 5/1982 | Haugwitz | 544/140 |
| 4,371,699 | 2/1983 | Ohashi et al. | 548/201 |
| 4,483,850 | 11/1984 | Patchett et al. | 424/177 |
| 4,513,009 | 4/1985 | Roques et al. | 514/513 |
| 4,524,212 | 6/1985 | Gordon et al. | 548/533 |
| 4,602,002 | 7/1986 | Patchett et al. | 514/11 |
| 4,749,688 | 6/1988 | Haslanger et al. | 514/19 |
| 5,136,076 | 8/1992 | Duhamel et al. | 558/254 |
| 5,312,826 | 1/1994 | Nunami et al. | 514/371 |

FOREIGN PATENT DOCUMENTS

| | | |
|---|---|---|
| 0079464 | 5/1983 | European Pat. Off. |
| 274234 | 7/1987 | European Pat. Off. |
| 0254032 | 4/1988 | European Pat. Off. |
| 0318377 | 5/1989 | European Pat. Off. |
| 0519738 | 12/1992 | European Pat. Off. |

OTHER PUBLICATIONS

Lefrancois et al., The Lancet, 336, 307 (1990).
Greenlee, Pharm. Res. vol. 4, p. 364 (1987).

*Primary Examiner*—Christine M. Nucker
*Assistant Examiner*—Benet Prickril
*Attorney, Agent, or Firm*—Birch, Stewart, Kolasch & Birch

[57] ABSTRACT

There is disclosed an indole-containing peptide represented by the formula (I):

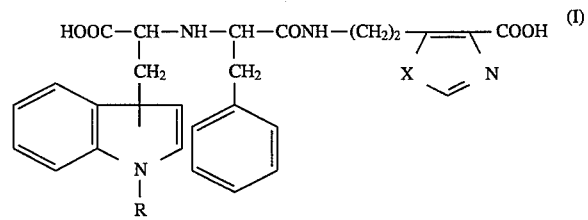

wherein R represents hydrogen atom, a lower alkyl group or formyl group; and X represents oxygen atom or sulfur atom, an ester thereof or pharmaceutically acceptable salts thereof.

13 Claims, No Drawings

INDOLE-CONTAINING PEPTIDE AND PROCESS FOR PREPARING THE SAME

BACKGROUND OF THE INVENTION

The present invention relates to a novel indole-containing peptide having an antihypertensive activity and/or heart failure curing activity and a process for preparing the same.

It has been known that atrial natriuretic peptide (ANP) secreted from atrial myocytes has strong diuretic, natriuretic and vasodilating activities and inhibitory activity on the renin-angiotensin-aldosterone system, and that ANP is effective for curing hypertension and heart failure. However, ANP itself is a polypeptide and poorly absorbed in the digestive tracts, so that its administration is limited to the parenteral route.

On the other hand, it has been known that ANP is inactivated by neutral metalloendopeptidase, and that the inhibitor of the enzyme can be used as a medicine for curing hypertension and/or heart failure because it increases the concentration of ANP in the blood.

SUMMARY OF THE INVENTION

An object of the present invention is to provide an indole-containing peptide having excellent neutral metalloendopeptidase inhibitory activity and being useful as an antihypertensive drug and/or a medicine for curing heart failure.

The present invention relates to an indole-containing peptide represented by the formula (I):

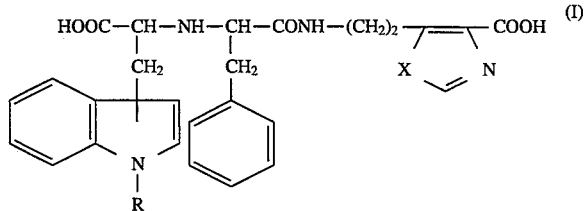

wherein R represents hydrogen atom, a lower alkyl group or formyl group; and X represents oxygen atom or sulfur atom, an ester thereof or pharmaceutically acceptable salts thereof, and also relates to a process for preparing the same.

DESCRIPTION OF THE PREFERRED EMBODIMENT

In the desired compound (I) of the present invention, a free carboxylic acid-type compound has excellent pharmaceutical activity, and an ester thereof is a prodrug which is hydrolyzed to be a free carboxylic acid-type compound exhibiting the activity through metabolism in vivo. In the desired compound (I) of the present invention, those in which R is hydrogen atom, methyl group or formyl group are preferred. Among them, those in which R is hydrogen atom are more preferable. Other preferred examples of the desired compound (I) are those in which X is oxygen atom. Other preferred examples of the desired compound (I) are those represented by the formula (I-a):

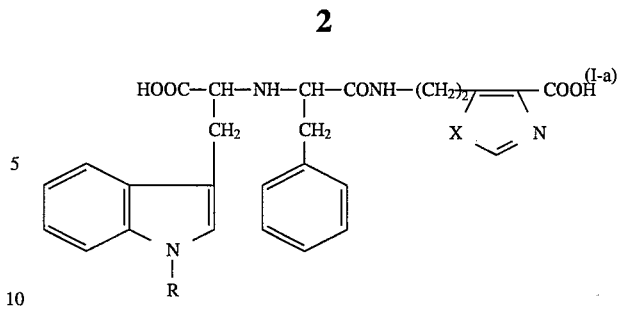

wherein the symbols have the same meaning as bove.

As the ester residue, there may be used any one which does not influence pharmaceutical effects of a free carboxylic acid-type compound when hydrolyzed in vivo, and is pharmaceutically acceptable. Such an ester residue may include an ester residue such as a lower alkyl ester, a halogen-substituted lower alkyl ester, a phenyl-lower alkyl ester or a phenacyl ester. As a specific example of the ester compound, there may be mentioned, for example, mono lower alkyl ester, di lower alkyl ester, mono(phenyl lower alkyl) ester, di (phenyl lower alkyl) ester and mono lower alkylmono (phenyl lower alkyl) ester. Among them, a preferred ester compound is a mono or di lower alkyl ester compound, and particularly preferred is a mono- or diethyl ester compound.

Further, as a pharmaceutically acceptable salt of the desired compound (I) of the present invention or an ester thereof, there may be mentioned, for example, an inorganic acid addition salt such as hydrobromide, hydrochloride, sulfate, phosphate and nitrate; an organic acid addition salt such as methanesulfonate, p-toluenesulfonate, oxalate, fumarate, maleate, tartrate and citrate; and an alkali metal salt such as sodium salt and potassium salt.

The desired compound (I) of the present invention includes 4 kinds of optically active isomers based on two asymmetric carbon atoms and a mixture thereof. Among them, those in which both of two asymmetric carbon atoms have S configurations (hereinafter referred to "(S—S) isomer") are pharmaceutically particularly preferred.

In the desired compound (I) of the present invention, the lower alkyl group means an alkyl group having 1 to 6 carbon atoms, preferably, an alkyl group having 1 to 4 carbon atoms.

The desired compound (I), an ester thereof or a salt thereof can be administered orally or parenterally, if necessary, in admixture with a conventional pharmaceutically acceptable carrier, diluent or disintegrant suitable for oral or parenteral administration. The pharmaceutical preparation may be either a solid preparation such as a tablet, a capsule and a powder or a liquid preparation such as a solution, a suspension and an emulsion. Further, in the case of parenteral administration, it may be also used as an injection.

The dose varies depending on an administration method, age, body weight and state of a patient and a kind of a disease to be cured, but, in general, it may be preferably about 1 to 100 mg/kg, particularly about 3 to 30 mg/kg per day.

According to the present invention, the desired compound (I) can be prepared by:

(1-a) carrying out condensation-reaction of a carboxylic acid compound represented by the formula (II):

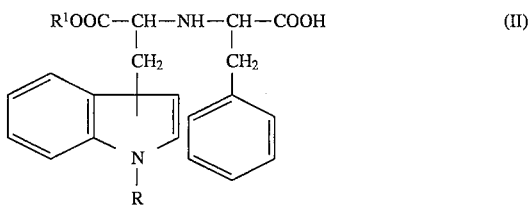
(II)

wherein $R^1$ represents a protective group for the carboxyl group; and R has the same meaning as above,
a salt thereof or a reactive derivative thereof in the carboxyl group, with an amine compound represented by the formula (III):

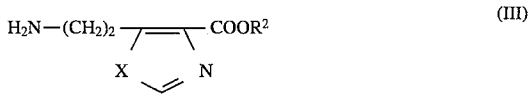
(III)

wherein $R^2$ represents a protective group for the carboxyl group; and X has the same meaning as above,
or a salt thereof, or (1-b) carrying out condensation-reaction of an indole compound represented by the formula (IV):

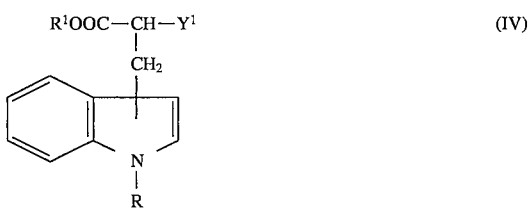
(IV)

wherein $Y^1$ represents a reactive residue or amino group; and the other symbols have the same meanings as above,
with a phenylalanine amide compound represented by the formula (V):

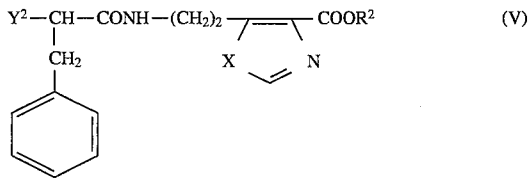
(V)

wherein $Y^2$ is amino group when $Y^1$ is a reactive residue, or $Y^2$ is a reactive residue when $Y^1$ is amino group; and the other symbols have the same meanings as above,
or a salt thereof, then (2) removing the protective groups $R^1$ and/or $R^2$, if desired, and (3) converting the resulting compound to an ester thereof or pharmaceutically acceptable salts thereof if further desired.

As the protective groups $R^1$ and $R^2$, there may be mentioned an ester residue such as a lower alkyl ester, a halogen-substituted lower alkyl ester, a phenyl-lower alkyl ester or a phenacyl ester. When the group $Y^1$ or $Y^2$ is a reactive residue, as the reactive residue, a substituted or non-substituted benzenesulfonyloxy group and a halogen atom may preferably be used.

As a salt of the carboxylic acid compound (II), an alkali metal salt and an alkaline earth metal salt may be suitably used, and as salts of the amine compound (III) and the phenylalanine amide compound (V), an inorganic acid salt such as a mineral acid salt and an organic acid salt may be suitably used.

The condensation reaction of the carboxylic acid compound (II) or a salt thereof and the amine compound (III) or a salt thereof may be carried out suitably in the presence of a dehydrating agent. As the dehydrating agent, any agent which can be used for synthesizing peptide may be used, and there may be mentioned, for example, water-soluble carbodiimide such as 1-ethyl-3-(3-dimethylaminopropyl)carbodiimide, and dicyclohexylcarbodiimide.

On the other hand, the condensation reaction of the reactive derivative in carboxyl group of the carboxylic acid compound (II) and the amine compound (III) or a salt thereof, and the condensation reaction of the indole compound (IV) and the phenylalanine amide compound (V) or a salt thereof may be carried out suitably in the presence or absence of an acid acceptor. As the acid acceptor, there may be used suitably any of an organic base such as tri-lower alkylamine, N,N-di-lower alkylamine or pyridine; and an inorganic base such as an alkali metal hydroxide, an alkali metal hydrogen carbonate, an alkali metal carbonate or an alkali metal hydride. As the reactive derivative in carboxyl group of the carboxylic acid compound (II), there may be used those conventionally used in synthesizing peptide, for example, any of an acyl halide, an active ester, mixed acid anhydride and azide.

These reactions are preferably carried out in the presence of an appropriate solvent such as dimethylformamide, hexamethylphosphoric triamide, tetrahydrofuran, dioxane, acetonitrile or a mixed solvent thereof or without solvent under cooling to room temperature, preferably at $-30°$ to $30°$ C.

From the thus obtained compound, the protective groups $R^1$ and/or $R^2$ can be removed according to an ordinary method such as catalytic hydrogenolysis and acidic hydrolysis, depending on the kind of the protective group. If required, the resultant compound can further be converted to an ester thereof or a pharmaceutically acceptable salt thereof according to an ordinary method.

The starting compounds (II), (III) and (V) in the present invention are novel compounds. The carboxylic acid compound (II) can be prepared by reacting the indole compound (IV) wherein $Y^1$ is amino group, with an aminoacetic acid compound represented by the formula (VI):

(VI)

wherein $Y^3$ represents a reactive residue; and $Z^1$ represents a protective group for the carboxyl group,
in the presence of an acid acceptor and then removing the protective group $Z^1$.

The amine compound (III) in which X is oxygen atom can be prepared by reacting, for example, an aminopropionic acid compound represented by the formula (VII):

$Z^2$—NH—(CH$_2$)$_2$—COOH (VII)

wherein $Z^2$ represents a protective group for the amino group,
with an isocyanoacetic acid compound represented by the formula (VIII):

CN—CH$_2$COOR$^2$ (VIII)

wherein R² has the same meaning as above, in the presence of an acid acceptor and then removing the protective group Z². The amine compound (III) in which X is sulfur atom can be prepared by subjecting the amine compound (III) wherein X is oxygen atom to ring opening reaction and treating the resulting compound with a sulfurizer such as 2,4-bis(4-methoxyphenyl)-1,3-dithia-2,4-diphosphetane- 2,4-disulfide. Also, the phenylalanine amide compound (V) can be prepared by subjecting a phenylpropionic acid compound represented by the formula (IX):

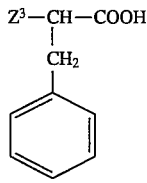
(IX)

wherein Z³ represents hydroxyl group or a protected amino group, or a reactive derivative in the carboxyl group, and the amine compound (III) to condensation-reaction according to an ordinary method, and then, by converting Z³ to a reactive residue by, for example, tosylation when Z³ is hydroxyl group, or removing the protective group when Z³ is a protected amino group.

Since the above mentioned reactions of the present invention proceed without accompanying racemization the desired compound (I) can be obtained as an optically active isomer by using an optically active starting materials.

The indole-containing peptide (I) which is the desired compound of the present invention, an ester thereof and a pharmaceutically acceptable salt thereof have excellent neutral metalloendopeptidase inhibitory activity, and exhibit excellent diuretic and vasodilating activities and inhibitory activity on renin and aldosterone secretion based on inhibiting effect of atrial natriuretic peptide (ANP) degradation. Thus, they can be used as a curing and/or prophylactic medicine for mammalia including human beings with hypertension, heart failure and renal insufficiency. Particularly for curing hypertension, angiotensin-converting enzyme inhibiting agents (ACE inhibiting agents) such as captopril and derapril hydrochloride have been clinically used at present. However, the desired product of the present invention, an ester thereof and pharmaceutically acceptable salts thereof have excellent characteristic that they have effects also on low renin hypertension while these ACE inhibiting agents have relatively small effects thereon.

EXAMPLES

The present invention is described in detail by referring to Examples, but the scope of the invention is not limited by these Examples.

Example 1

(1) A mixture comprising 3.5 g of (L)-tryptophan benzyl ester, 3.5 g of p-methoxybenzyl (2R)-3-phenyl-2-p-toluene-sulfonyloxypropionate, 2.1 ml of di (isopropyl) ethylamine and 5 ml of hexamethylphosphoric triamide was stirred at 70° C. for 20 hours. The reaction mixture was cooled and then added to an ethyl acetate-saturated sodium chloride mixed solution to separate an organic phase. The organic phase was washed and dried, the solvent was evaporated, and the resulting residue was purified by silica gel to give 2.6 g of N-((1S)-1-benzyloxycarboxyl-2-(3-indolyl)ethyl)-(L)-phenylalanine p-methoxybenzyl ester as an oily material.

NMR (CDCl₃) δ: 2.90 (d, 2H), 3.10 (m, 2H), 3.61 (t, 1H), 3.71 (t, 1H), 3.78 (s, 3H), 4.82 (s, 2H), 4.98 (s, 2H), 6.77 to 7.56 (m, 19H), 7.88 (s, 1H).

(2) A mixture comprising 0.44 g of the above obtained product, 10 ml of trifluoroacetic acid and 0.5 ml of anisole was stirred at a room temperature for one hour, and the solvent was evaporated. Then, the residue was added to an ethyl acetate-saturated sodium hydrogencarbonate mixed solution. pH of the mixture was adjusted to about 6.5 with citric acid and the organic phase was separated. The organic phase was washed and dried, the solvent was evaporated, and the residue was solidified by ethanol-hexane and filtered to give 290 mg of N-((1S)-1-benzyloxycarbonyl-2-( 3-indolyl)ethyl)-(L)-phenylalanine.

M.P.: 147° to 150° C. NMR (CDCl₃) δ: 2.85 to 3.60 (m, 5H), 3.78 (t, 1H), 5.02 (m, 2H) , 6.82 to 7.45 (m, 15H) , 8.03 (bs, 1H).

(3) To 3 ml of dimethylformamide were added 270 mg of the thus obtained product, 300 mg of 4-benzyloxycarbonyl-5-(2 -aminoethyl)oxazole hydrobromide and 95 mg of 1-hydroxy-benzotriazole monohydrate, and under cooling, 140 mg of 1 -ethyl-3-(3-dimethylaminopropyl)carbodiimide hydrochloride and 0.14 ml of triethylamine were added to the mixture. Then, the mixture was stirred at room temperature for 3 hours. The solvent was evaporated under reduced pressure. Ethyl acetate was added to the residue and the mixture was washed and dried. Then, the solvent was evaporated and the residue was purified by silica gel to give 270 mg of 4 -benzyloxycarbonyl-5-{2-[N-((1S)-1-benzyloxycarbonyl-2-(3 -indolyl)ethyl)-(L)-phenylalanyl] aminoethyl}oxazole as an oily product.

NMR (CDCl₃) δ: 2.22 to 2.34 (m, 1H), 2.50 to 2.75 (m, 3H), 2.93 to 3.35 (m, 6H), 5.02 (m, 2H), 5.43 (s, 2H), 6.46 (bt, 1H), 6.90 to 7.55 (m, 19H), 7.68 (s, 1H), 8.30 (bs, 1H).

Examples 2 to 3

(1) Corresponding starting compounds were treated in the same manner as in Example 1-(1) to give compounds listed in Table 1 below.

TABLE 1

$$R^1OOC-CH-NH-CH-COOA$$
$$\phantom{R^1OOC-}|\phantom{CH-NH-}|$$
$$\phantom{R^1OOC-}CH_2\phantom{NH-}Bzl$$

(indol-3-ylmethyl group on the CH₂, with N–R on indole nitrogen)

| Example No. | R¹ | R | A | Physical properties |
|---|---|---|---|---|
| 2-(1) | —CH₂CH₃ | H | Bzl | State: syrup<br>NMR (CDCl₃) δ:<br>1.09 (t, 3H)<br>2.92 to 3.22 (m, 4H)<br>3.61 to 3.69 (m, 2H)<br>4.02 (m, 2H)<br>4.87 (m, 2H)<br>6.99 to 7.57 (m, 15H)<br>7.94 (bs, 1H) |
| 3-(1) | Bzl | CHO | —CH₂—C₆H₄—OCH₃ | State: syrup<br>NMR (CDCl₃) δ:<br>2.7 to 3.3 (m, 4H)<br>3.5 to 3.9 (m, 3H)<br>3.78 (s, 3H)<br>4.8 to 5.2 (m, 4H)<br>6.5 to 7.6 (m, 18H)<br>8.2 to 8.8 (m, 2H) |

Note 1: Bzl represents benzyl group (hereinafter, abbreviated in the same manner).
(2) The above obtained compounds were treated in the same manner as in Example 1-(2) to 1-(3) to give compounds listed in Table 2 below.

TABLE 2

$$R^1OOC-CH-NH-CH-CONH-(CH_2)_2-\text{(heterocycle)}-COOR^2$$
$$\phantom{R^1OOC-}|\phantom{CH-NH-}|\phantom{CH-CONH-(CH_2)_2-}X\phantom{-COO}N$$
$$\phantom{R^1OOC-}CH_2\phantom{NH-}Bzl$$

(indol-3-ylmethyl on CH₂, with N–R on indole)

| Example No. | R¹ | R | X | R² | Physical properties |
|---|---|---|---|---|---|
| 2-(2) | —CH₂CH₃ | H | O | Bzl | State: syrup<br>NMR (CDCl₃) δ:<br>1.18 (t, 3H)<br>2.12 to 2.28 (m, 1H)<br>2.53 to 3.27 (m, 9H)<br>4.04 (m, 2H)<br>5.43 (s, 2H)<br>6.43 (bt, 1H)<br>6.96 to 7.53 (m, 15H)<br>7.70 (s, 1H)<br>8.40 (bs, 1H) |
| 3-(2) | Bzl | CHO | O | Bzl | State: syrup<br>NMR (CDCl₃) δ:<br>2.0 (br, 1H)<br>2.5 to 3.5 (m, 10H)<br>4.7 to 5.5 (m, 4H)<br>6.65 to 7.7 (m, 20H)<br>8.2 to 9.4 (m, 2H) |

Examples 4 to 5

Corresponding starting compounds were treated in the same manner as in Example 1 to give compounds listed in Table 3 below.

TABLE 3

R¹OOC—CH—NH—CH—CONH—(CH₂)₂—⟨oxazole/thiazole ring with X, N⟩—COOR²
  |           |
  CH₂         Bzl
  |
  [indole with N-R]

| Example No. | R¹ | R | X | R² | Physical properties |
|---|---|---|---|---|---|
| 4 | Bzl | H | O | —CH$_2$CH$_3$ | State: syrup<br>NMR (CDCl$_3$) δ:<br>1.44 (t, 3H)<br>2.28 to 2.44 (m, 1H)<br>2.58 to 2.79 (m, 4H)<br>2.97 to 3.33 (m, 5H)<br>4.45 (m, 2H)<br>5.01 (m, 2H)<br>6.51 (bt, 1H)<br>6.98 to 7.52 (m, 15H)<br>7.68 (s, 1H)<br>8.52 (bs, 1H) |
| 5 | Bzl | H | S | —CH$_2$CH$_3$ | State: syrup<br>NMR (CDCl$_3$) δ:<br>1.48 (t, 3H)<br>2.27 to 2.39 (m, 1H)<br>2.61 to 3.40 (m, 10H)<br>4.50 (m, 2H)<br>5.02 (m, 2H)<br>6.55 (bt, 1H)<br>6.92 to 7.51 (m, 15H)<br>8.40 (bs, 1H)<br>8.60 (s, 1H) |

Example 6

(1) To 30 ml of dimethylformamide solution containing 1.67 g of (2R)-2-hydroxy-3-phenylpropionic acid, 3.29 g of 4-benzyloxycarbonyl-5-(2-aminoethyl)oxazole monohydrobromide and 1.62 g of 1-hydroxybenzotriazole monohydrate were added 1.54 ml of triethylamine and 2.12 g of 1-ethyl-3-(3-dimethylaminopropyl)carbodiimide hydrochloride at −20° C. and the mixture was stirred at room temperature overnight.

After the solvent was removed by evaporation, ethyl acetate was added to the residue, and the mixture was washed and dried. Then, the solvent was removed by evaporation, and the resulting residue was crystallized from hexane to give 3.80 g of 4-benzyloxycarbonyl-5-{2-((2R)-2-hydroxy-3-phenylpropionyl)aminoethyl}oxazole.

M.P.: 106° to 108° C. NMR (CDCl$_3$) δ: 2.70 to 2.91 (m, 2H), 3.12 to 3.25 (m, 3H), 3.43 to 3.67 (m, 2H), 4.17 (m, 1H), 5.39 (s, 2H), 6.86 (bt, 1H), 7.16 to 7.45 (m, 10H), 7.70 (s, 1H)

(2) To the thus obtained product (3.1 g) dissolved in 9 ml of pyridine was added 1.50 g of p-toluenesulfonyl chloride and the mixture was stirred at room temperature overnight. Ethyl acetate was added to the mixture, and the mixture was washed and dried. Then, the solvent was removed by evaporation and the resulting residue was crystallized from hexane to give 3.7 g of 4-benzyloxycarbonyl-5-{2-((2R)-2 -p-toluenesulfonyloxy-3-phenylpropionyl)aminoethyl}oxazole.

M.P.: 96° to 98° C. NMR (CDCl$_3$) δ: 2.40 (s, 3H), 2.86 to 3.30 (m, 4H), 3.47 to 3.56 (m, 2H), 4.89 to 4.95 (m, 1H), 5.37 (s, 2H), 6.60 (bt, 1H), 6.94 to 7.51 (m, 14H), 7.70 (s, 1H)

(3) In the same manner as in Example 1-(1) by treating the corresponding starting compounds, from 1.64 g of the thus obtained product and 920 mg of (L)-1-methyltryptophan benzyl ester under, 1.5 g of 4-benzyloxycarbonyl-5-{2-[N-((1S)-1-benzyloxycarbonyl-2-(1-methyl-3-indolyl)ethyl)-(L)-phenylalanyl]aminoethyl}oxazole was obtained.

M. P.: 68° C. (decomposed) NMR (CDCl$_3$) δ: 2.40 to 2.83 (m, 5H), 2.96 to 3.40 (m, 5H), 3.64 (s, 3H), 4.98 (m, 2H), 5.36 (s, 2H), 6.61 (bt,1H), 7.01 to 7.49 (m, 22H), 7.64 (s, 1H)

Example 7

1.1 g of 4-benzyloxycarbonyl-5-{2-[N-((1S)-1 -benzyloxy-carbonyl-2-(3-indolyl)ethyl)-(L)-phenylalanyl]aminoethyl}oxazole was subjected to catalytic hydrogenolysis in 20 ml of dimethylformamide in the presence of 100 mg of palladium black. The reaction is carried out at room temperature at 3 atmospheric pressure for 3 hours. After removal of the catalyst by filtration, the solvent was removed by evaporation and the resulting residue was crystallized from isopropyl ether to give 865 mg of 4-carboxy-5-{2-[N-((1S)-1 -carboxy-2-(3-indolyl)ethyl)-(L)-phenylalanyl]aminoethyl}oxazole.

M.P.: 77° C. (decomposed) NMR (DMSO-d$_6$) δ: 2.80 to 3.70 (m, 10H), 6.93 to 7.53 (m, 14H), 8.26 (s, 1H), 10.9 (bs, 1H)

Examples 8 to 12

The compounds prepared in Examples 2 to 6 were treated in the same manner as in Example 7 to give compounds listed in Table 4 below.

TABLE 4

$$R^1OOC-CH(CH_2\text{-indolyl-}NR)-NH-CH(Bzl)-CONH-(CH_2)_2-\text{thiazole}(X,N)-COOR^2$$

| Example No. | $R^1$ | R | X | $R^2$ | Physical properties |
|---|---|---|---|---|---|
| 8 | $-CH_2CH_3$ | H | O | H | m.p.: 89° C. (decomposed)<br>NMR (DMSO-$d_6$) δ:<br>1.95 (t, 3H)<br>2.73 to 3.50 (m, 10H)<br>3.85 (m, 2H)<br>6.92 to 7.48 (m, 11H)<br>8.27 (s, 1H)<br>10.9 (bs, 1H) |
| 9 | H | CHO | O | H | m.p.: 128 to 130° C. (decomposed)<br>NMR (DMSO-$d_6$) δ:<br>2.2 to 3.9 (m, 9H)<br>6.7 to 8.4 (m, 11H)<br>8.9 to 9.6 (m, 2H) |
| 10 | H | H | O | $-CH_2CH_3$ | m.p.: 77° C. (decomposed)<br>NMR (DMSO-$d_6$) δ:<br>1.27 (t, 3H)<br>2.70 to 3.67 (m, 10H)<br>4.24 (m, 2H)<br>6.92 to 7.53 (m, 10H)<br>8.31 (s, 1H)<br>10.9 (bs, 1H) |
| 11 | H | H | S | $-CH_2CH_3$ | m.p.: 93° C. (decomposed)<br>NMR (DMSO-$d_6$) δ:<br>1.29 (t, 3H)<br>2.85 to 3.80 (m, 10H)<br>4.27 (m, 2H)<br>6.94 to 7.52 (m, 10H)<br>8.89 (s, 1H)<br>11.0 (bs, 1H) |
| 12 | H | $CH_3$ | O | H | m.p.: 68° C. (decomposed)<br>NMR (DMSO-$d_6$) δ:<br>2.70 to 3.65 (m, 10H)<br>3.72 (s, 3H)<br>6.95 to 7.53 (m, 11H)<br>8.28 (s, 1H) |

Example 13

A mixture comprising 535 mg of the product prepared in Example 11, 4-ethoxycarbonyl-5-{2-[N-((1S)-1-carboxy-2-(3-indolyl)ethyl)-(L)-phenylalanyl]aminoethyl}thiazole, 1.5 ml of 2N sodium hydroxide solution and 2 ml of methanol was stirred for 2 hours under ice-cooling. After the solvent was removed by evaporation, 1.5 ml of 2N hydrochloric acid solution was added to the residue. The obtained solid was collected by filtration and washed successively with water and then ether to give 285 mg of 4-carboxy-5-{2-[N-((1S)-1-carboxy-2-(3-indolyl)ethyl)-(L)-phenylalanyl]aminoethyl}thiazole.

M.P.: 131° C. NMR (DMSO-$d_6$) δ: 2.65 to 3.65 (m, 10H), 6.91 to 7.53 (m, 11H), 8.88 (s, 1H), 10.9 (bs, 1H)

We claim:

1. An indole-containing peptide represented by the formula (I):

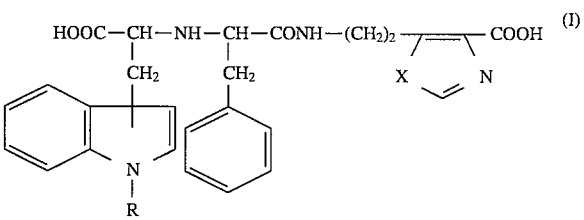

wherein R represents a hydrogen atom, a lower alkyl group or formyl group; and X represents an oxygen atom or sulfur atom, an ester thereof or a pharmaceutically acceptable salt thereof.

2. The indole-containing peptide according to claim 1, wherein R represents a hydrogen atom, an alkyl having 1 to 6 carbon atoms or a formyl group.

3. The indole-containing peptide according to claim 1, wherein R is a hydrogen atom, methyl group or formyl group.

4. The indole-containing peptide according to claim 1, which is a mono- or di-lower alkyl ester.

5. The indole-containing peptide according to claim 1, which is a monoethyl ester or a diethyl ester.

6. The indole-containing peptide according to claim 1, wherein both of two asymmetric carbon atoms have S configurations.

7. The indole-containing peptide according to claim 1, which is a salt selected from a hydrobromide, a hydrochloride, a sulfate, a phosphate, a nitrate, a methanesulfonate, a p-toluenesulfonate, an oxalate, a fumarate, a maleate, a tartrate, a citrate, a sodium salt or a potassium salt.

8. 4-Carboxy-5-{2-[N((1S)-1-carboxy-2-(3-indolyl-)ethyl)-(L)-phenylalanyl]aminoethyl}oxazole, a mono- or di-ethyl ester thereof or a pharmaceutically acceptable salt thereof.

9. A pharmaceutical composition which comprises the compound according to any one of claims 1–8 and 11–14 in admixture with a conventional pharmaceutically acceptable carrier, diluent or disintegrant therefor.

10. The indole-containing peptide according to claim 1, wherein R is H, —CHO or —CH$_3$.

11. The ester of the indole-containing peptide according to claim 10.

12. The indole-containing peptide according to claim 1, wherein R is H, and X is O.

13. The mono-ethyl ester of the indole-containing peptide according to claim 12.

* * * * *